(12) United States Patent
Park et al.

(10) Patent No.: US 11,519,017 B2
(45) Date of Patent: Dec. 6, 2022

(54) **KIT FOR DIAGNOSING INFECTION WITH METHICILLIN-RESISTANT *STAPHYLOCOCCUS AUREUS* (MRSA) BY DETECTING MAGNESIUM IONS**

(71) Applicant: Bioacts Corporation, Incheon (KR)

(72) Inventors: Jin Woo Park, Incheon (KR); Jae-Ho Choi, Incheon (KR); Bongkyu Lee, Siheung (KR); Hyoung Su Kim, Ansan (KR); Kiwon Kim, Incheon (KR); Jae-Sung Lee, Wonju (KR); Hyo Sung Jeon, Daegu (KR); Sora Yun, Daegu (KR)

( * ) Notice: Subject to any disclaimer, the term of this patent is extended or adjusted under 35 U.S.C. 154(b) by 709 days.

(21) Appl. No.: 16/345,700

(22) PCT Filed: Dec. 21, 2018

(86) PCT No.: PCT/KR2018/016462
§ 371 (c)(1),
(2) Date: Apr. 27, 2019

(87) PCT Pub. No.: WO2019/132444
PCT Pub. Date: Jul. 4, 2019

(65) Prior Publication Data
US 2021/0355521 A1 Nov. 18, 2021

(30) Foreign Application Priority Data
Dec. 26, 2017 (KR) .......................... 10-2017-0179022

(51) Int. Cl.
| | | |
|---|---|---|
| *C12Q 1/14* | (2006.01) | |
| *C09B 29/02* | (2006.01) | |
| *C09B 29/30* | (2006.01) | |
| *C09B 29/46* | (2006.01) | |
| *C12Q 1/6844* | (2018.01) | |
| *G01N 33/84* | (2006.01) | |

(52) U.S. Cl.
CPC .............. *C12Q 1/14* (2013.01); *C09B 29/02* (2013.01); *C09B 29/30* (2013.01); *C09B 29/3652* (2013.01); *C12Q 1/6844* (2013.01); *G01N 33/84* (2013.01); *G01N 2333/31* (2013.01)

(58) Field of Classification Search
CPC ..... C09B 29/02; C09B 29/30; C09B 29/3652; C12Q 1/14; C12Q 1/6844; G01N 2333/31; G01N 33/84
See application file for complete search history.

(56) References Cited

U.S. PATENT DOCUMENTS 7,888,532 B2    2/2011   Cho

FOREIGN PATENT DOCUMENTS

| GB | 2202232 B | * | 3/1991 | .......... C09B 41/004 |
|---|---|---|---|---|
| KR | 10-0858560 B1 | | 9/2008 | |
| KR | 10-1329316 B1 | | 11/2013 | |
| KR | 10-1552159 B1 | | 9/2015 | |
| KR | 200180041883 A | * | 1/2018 | ............. C09B 29/02 |
| KR | 10-1908869 B1 | | 10/2018 | |

OTHER PUBLICATIONS

Misawa et al. J. Infectious Chemotherap. (2007) 13:143-140 (Year: 2007).*
Katayama et al. Bulletin Chem. Soc. Japan (1971) 44: 3040-3043 (Year: 1971).*
Machine translation of KR 20180041883 A; published Apr. 25, 2018, to Parkd et al. downloaded from Dialog Nov. 16, 2021 (Year: 2018).*
Compound Registry No. 757143-73-0 added to the Registry file Oct. 3, 2014; downloaded from STN Nov. 17, 2021 (Year: 2004).*
Compound Registry No. 1407097-18-0 added to the Registry File Nov. 26, 2012; downloaded from STN Nov. 17, 2021 (Year: 2012).*
Compound Registry No. 743387-63-5 added to the Registry File Sep. 4, 2005; downloaded from STN Nov. 17, 2021 (Year: 2004).*
International Search Report dated Apr. 19, 2019 for PCT/KR2018/016462.
Goto, Motoki et al., "Colorimetric detection of loop-mediated isothermal amplification reaction by using hydroxy naphthol blue," Biotechniques, Mar. 2009., vol. 46, No. 3, pp. 167-172.
Diehl, Harvey et al., "Azo Dyes as Indicators for Calcium and Magnesium," Anal. Chem., 1960, vol. 32, No. 9, pp. 1120-1123.
Cacho, Juan et al., "Comparative study of metallochromic indicators for magnesium," ANALYST, Dec. 1987, vol. 112, pp. 1723-1728.
Yoshiki Misawa et al. 2007, Application of loop-mediated isothermal 15 amplification technique to rapid and direct detection of methicillin-resistant *Staphylococcus aureus* in blood cultures. J infect Chemother, 13:134-14.

* cited by examiner

*Primary Examiner* — Susan M Hanley (57) ABSTRACT

Provided is a diagnostic kit for determining infection with Methicillin-Resistant *Staphylococcus aureus* (MRSA) in a specimen, and a method for determining the infection with MRSA using the diagnostic kit is performed by visually observing a color change after LAMP reaction, and the color change is caused by a change in a magnesium concentration and confirmed using a specific dye compound which sensitively reacts with magnesium ions. The amplification of the MRSA DNA is performed using the loop-mediated isothermal amplification (LAMP), so that the diagnostic kit has advantages of being conveniently used anytime and anywhere and quickly diagnosing.

3 Claims, 3 Drawing Sheets

KIT FOR DIAGNOSING INFECTION WITH METHICILLIN-RESISTANT *STAPHYLOCOCCUS AUREUS* (MRSA) BY DETECTING MAGNESIUM IONS

STATEMENT AS TO GOVERNMENT SPONSORED RESEARCH

This research was financially supported by the Ministry of Trade, Industry, and Energy (MOTIE), the Republic of Korea, under the Support Program for Regional Industry-based Organizations (Project No. R0006231) supervised by the Korea Institute for Advancement of Technology (KIAT).

CROSS REFERENCE TO RELATED APPLICATIONS

This application claims priority to Korean Patent Application No. 10-2017-017902, filed on Dec. 26, 2017. Further, the application is the National Phase application of International Application No. PCT/KR2018/016462, filed on Dec. 21, 2018, which designates the United States. Each of these applications is hereby incorporated by reference in their entirety into the present application.

BACKGROUND

Technical Field

Embodiments of the present invention relate to a diagnostic kit capable of simply determining infection with Methicillin-resistant *Staphylococcus aureus*(MRSA) by visually confirming a change in the concentration of divalent magnesium ions ($Mg^{2+}$) generated in loop-mediated isothermal amplification (LAMP) using a dye compound when determining the infection with MRSA in a specimen.

Related Art

Recently, in a bio-diagnosis field, the market for a point of care test (POCT), which is a diagnostic system that enables a rapid spot test without expensive equipments, is rapidly growing, and a lot of contents in which existing genetic tests and molecular diagnostic kits are applied to new platforms have been developed to have this market competitiveness.

Diagnostic methods which have been mainly used currently include a bacterial culture identification method, a PCR and a sequencing method, and a POCT which directly measures bacteria. However, high-level equipments and a lot of manpower are required based on a diagnostic Lab according to detection.

Methicillin-resistant *Staphylococcus aureus* (MRSA) is bacteria mainly causing hospital-acquired infection such as wound infections, pneumonia, and sepsis. The MRSA is multiple drug resistant bacteria which are resistant to all β-lactam agents such as penicillin, cephalosporin, and carbapenem due to altered penicillin binding proteins (PBP 2a, PBP 2') mainly generated by a mecA gene and resistant even to other types of antimicrobial agents such as macrolide, clindamycin, tetracycline, and aminoglycoside. Accurate and rapid bacterial identification and an antimicrobial susceptibility test are required for the selection of appropriate antimicrobial agents and management of hospital-acquired infection.

As the accurate identification method of the MRSA, there are a method of directly detecting a mecA gene using a DNA probe or a polymerase chain reaction (PCR) as a molecular biological test method, a method of detecting a product of the mecA gene, PBP 2a using immunoblotting or immuno-radiometric assay (IRMA), and the like. However, various conditions such as special equipments, expensive reagents, and complicated test counts and test time are not suitable to be used generally in general laboratories, and an antimicrobial susceptibility test, which has been traditionally used, requires an incubation time of 24 hours and has a difference in the expression of resistance depending on a type of culture medium or a culture condition, so that it is difficult to expect rapid and accurate results.

In the case of a POCT method for directly measuring these bacteria, there is a problem that the high cost and the sensitivity and accuracy of the test results do not reach a reliable level. Recently, to overcome the problem, a technique suitable for pathogen detection using loop-mediated isothermal amplification (LAMP) has been proposed.

The polymerase chain reaction (PCR) in the related art requires three temperature changes: denaturation, annealing, and extension. However, in the loop-mediated isothermal amplification (LAMP), since the DNA amplification reaction occurs at one temperature, there is no need for a separate special machine (PCR machine) like polymerase chain reaction.

In the LAMP, since a target nucleic acid may be amplified to $10^9$ copies within 1 hour at 60 to 65° C., measuring is enabled only with a constant temperature keeping device at about 64 to 65° C., a test time is as short as 30 to 60 minutes, observation is enabled visually, and it is unnecessary to acquire specialized knowledge required for purchasing expensive equipment and operating equipment, thereby simply and easily amplifying DNA.

The method is based on autocycling strand displacement DNA synthesis by a DNA polymerase with strong strand displacement activity, in which the test itself is very simple because the reaction occurs under isothermal conditions and the amplification efficiency is very high because there is no time loss in temperature change. As such, in the case of the diagnostic method using the isothermal amplification, since a very small amount of DNA is more efficiently synthesized than the general PCR in a short time, DNA is directly detected or byproducts are detected after DNA amplification to be used as a diagnostic kit.

On the other hand, magnesium ions ($Mg^{2}\pm$) are bivalent metal ions present in the most abundant amount in the cell, are known to not only participate in the regulation of several hundred enzyme activities, but also act as an important factor for DNA synthesis, and play a key role in many cellular processes such as cell proliferation and death. In order to detect such intracellular magnesium ions, a method of detecting magnesium ions using a confocal microscope having various cell-permeable phosphors and a one-photon or two-photon fluorescence probe has been proposed.

However, the above-described methods have a problem in that detection is enabled only by using expensive equipment. Therefore, it is required to develop a high-sensitive magnesium ion indicator which can be visually observed so as to be easily used for other researches other than the diagnostic kit and cell experiments related to magnesium.

The present invention is directed to provide a kit capable of detecting MRSA with high efficiency even in the presence of a minute amount of DNA and confirming the detected MRSA visually using loop-mediated isothermal amplification (LAMP) by using a method for detecting a change in magnesium concentration according to a color change of a dye compound when diagnosing Methicillin-resistant

*Staphylococcus aureus* (MRSA) as bacteria which are infected to humans to cause various diseases.

Technical Problems

An object of the present invention is to provide a kit for detecting Methicillin-resistant *Staphylococcus aureus* (MRSA), bacteria which are infected in humans to cause various diseases. In order to detect MRSA bacteria, in the present invention, a novel dye compound capable of visually confirming a change in the concentration of magnesium ions has been developed.

A first object of the present invention is to provide a dye compound for detecting magnesium ions capable of visually confirming the presence of magnesium ions.

A second object of the present invention is to provide a method for quantifying magnesium ions using the dye compound for detecting magnesium ions.

A third object of the present invention is to provide a diagnostic kit capable of confirming DNA amplification using the dye compound for detecting magnesium ions when amplifying DNA using loop-mediated isothermal amplification (LAMP).

Further, the kit for detecting the MRSA bacteria developed in accordance with exemplary embodiments of the present invention is a kit for testing the infection with bacteria by detecting a change in magnesium concentration through a change in color of the dye compound, and general LAMP primers such as a primer of a mecA gene used in a kit for detecting MRSA by a molecular biological method may all be used.

PRIOR ART DOCUMENTS

Korean Patent Registration No. 10-0858560
Korean Patent Registration No. 10-1552159
Korean Patent Registration No. 10-1329316
Yoshiki Misawa et al. 2007, Application of loop-mediated isothermal amplification technique to rapid and direct detection of methicillin-resistant *Staphylococcus aureus* in blood cultures. J infect Chemother, 13:134-14

Technical Solutions

In order to solve the problems, exemplary embodiments of the present invention provide a dye compound for detecting magnesium ions represented by the following [Chemical Formula 1].

[Chemical Formula 1]

In Chemical Formula 1 above, $R_1$ and $R_2$ are selected from hydrogen, hydroxy and amino ($-NH_2$), $R_1$ or $R_2$ is hydroxy, wherein if $R_1$ is hydroxy, $R_2$ is hydrogen or amino, and if $R_2$ is hydroxy, $R_1$ is amino; $R_3$ is hydrogen;

$R_4$ is selected from hydrogen, $-NHRa$, and a sulfonic acid group, wherein Ra is selected from hydrogen, C1-6 alkyl, and phenyl; $R_5$ and $R_6$ are hydrogen or a sulfonic acid group, wherein if any one of $R_5$ and $R_6$ is a sulfonic acid group, the other one is hydrogen;

Ar is phenyl or naphthyl, wherein 1 to 3 hydrognes of the phenyl or naphthyl are substituted with a substituent selected from hydroxy, nitro, a sulfonic acid group, and halogen and at least one substituent of the phenyl or naphthyl is a hydroxy group, and the at least one hydroxy group is substituted with carbon at position 2; and the sulfonic acid group is sulfonic acid ($-SO_3H$) or sulfonic acid sodium salt ($-SO_3Na$).

In the dye compound for detecting magnesium ions according to embodiments of the present invention, in order to develop color by reacting with magnesium ions, one hydroxy group may need to be contained in the naphthyl group of [Chemical Formula 1,] and one or more of $R_1$ and $R_2$ may be a hydroxy group. When $R_1$ or $R_2$ is a hydroxy group, the hydroxy group reacts with magnesium ions and plays a major role in developing a color distinguishable from an original color.

In accordance with exemplary embodiments of the present invention, $R_3$ is H and important to improve the solubility of the dye compound according to the present disclosure. When $R_3$ is substituted with a substituent such as amine, the water solubility is not very good and the reaction with magnesium ions is not easy.

In accordance with exemplary embodiments of the present invention, $R_4$ is selected from hydrogen, $-NHRa$, and a sulfonic acid group, and may be $-NHRa$ or a sulfonic acid group, and more specifically $-NHRa$. When $R_4$ is $-NHRa$ or a sulfonic acid group, it is effective to be developed in a complementary color. Herein, Ra may be selected from hydrogen, C1-C6 alkyl and phenyl, specifically hydrogen or phenyl.

In accordance with exemplary embodiments of the present invention, any one of $R_5$ and $R_6$ may be a sulfonic acid group, and the other one may be hydrogen. Specifically, $R_5$ is a sulfonic acid group and $R_6$ is hydrogen, which is effective to react with magnesium ions to be developed in a complementary color.

In accordance with exemplary embodiments of the present invention, Ar in a mother nucleus of [Chemical Formula 1] is phenyl or naphthyl, and the phenyl or naphthyl may have 1 to 3 substituents. Here, a hydroxy group is specifically substituted in carbon at position 2 of Ar (phenyl or naphthyl), and more specifically, [Chemical Formula 1] may be represented by the following [Chemical Formula 1a].

[Chemical Formula 1a]

In [Chemical Formula 1a], $R_1$, $R_2$, $R_3$, $R_4$, $R_5$, and $R_6$ are the same as represented in [Chemical Formula 1] above, and $R_7$ and $R_8$ are the same as or different from each other and may be each independently selected from hydrogen, nitro, hydroxy, halogen and a sulfonic acid group.

According to exemplary embodiments of the present invention, $R_7$ and $R_8$ may be the same as or different from each other, and at least one of $R_7$ and $R_8$ may be any one selected from nitro, hydroxy, and a sulfonic acid group, and specifically, if at least one of $R_7$ and $R_8$ is nitro, at least one of $R_7$ and $R_8$ may be developed in a clearly distinguishable color or a complementary color by reacting with magnesium ions.

The compound represented by [Chemical Formula 1] according to exemplary embodiments of the present invention reacts with magnesium ions to be shifted to a different wavelength before reacting with magnesium ions, and has a difference in color developed depending on the position and intensity of the shifted wavelength. In addition, since there is a difference in wavelength shifted depending on the substituent of the compound, different colors are developed.

In addition, since the compound of [Chemical Formula 1] according to exemplary embodiments of the present invention is not developed by a change in pH in the absence of magnesium ions or developed to a different color from a color developed by magnesium ions so as not to be influenced by the change in pH, the compound is easily used without requiring pH adjustment and may be applied to a specimen without pH adjustment to detect magnesium ions contained in the specimen, and the detection is enabled by visual observation such as colorimetry or absorbance spectrophotometry, so that it is advantageous for industrial application.

The compound represented by [Chemical Formula 1] according to exemplary embodiments of the present invention may specifically be, for example, compounds represented by the following [Chemical Formula 2] to [Chemical Formula 10], but is not limited thereto.

[Chemical Formula 2]

[Chemical Formula 3]

[Chemical Formula 4]

[Chemical Formula 5]

[Chemical Formula 6]

[Chemical Formula 7]

[Chemical Formula 8]

[Chemical Formula 9]

[Chemical Formula 10] Compound DKLS

The compound of [Chemical Formula 1] according to exemplary embodiments of the present invention may be color-developed in the presence of 1 mM to 200 mM of magnesium ions, and has a difference in critical concentration of detectable magnesium ions and developed color depending on a difference in substituent. For example, the compound of [Chemical Formula 4] can be color-developed even in the presence of magnesium ions at a concentration of 3 mM or less, but other compounds are not color-developed at a concentration of magnesium ions of less than 8 mM. Since the developed color and the detectable critical concentration vary depending on the substituent of the compound, the amount of magnesium ions contained in the specimen to be detected may be quantified visually by using a plurality of dye compounds having different critical concentrations.

Exemplary embodiments of the present invention provide a magnesium ion detection kit comprising the dye compound of the [Chemical Formula 1]. Even though the detection kit contains only a type of dye compound, the detection is sufficiently enabled to confirm only the concentration of magnesium ions. On the other hand, it is possible to quantify magnesium ions contained in a specimen to be detected by using a kit containing a plurality of dye compounds having different detectable critical concentrations of magnesium ions.

A method of quantifying visually the presence of magnesium ions according to the present invention includes steps of administering and reacting 2 to 9 types of dye compounds selected from compounds represented by Chemical Formulas 2 to 10 to a specimen to be de detected; and confirming a color change.

Exemplary embodiments of the present invention also provide a diagnostic kit capable of visually checking DNA amplification by including a dye compound represented by [Chemical Formula 7]. In particular, exemplary embodiments of the present invention provide a kit for checking the amplification of DNA of methicillin-resistant *Staphylococcus aureus* (MRSA) by loop-mediated isothermal amplification (LAMP). In the related art, it is impossible to visually confirm DNA amplification.

By adding and reacting MRSA DNA to a loop-mediated isothermal amplification (LAMP) reaction solution containing the compound of [Chemical Formula 7] according to exemplary embodiments of the present invention, it is possible to visually confirm DNA amplification by a color change without using a detection machine.

Advantageous Effects

Since the dye compound for detecting magnesium ions according to exemplary embodiments of the present invention is stable to changes in temperature and pH and color-developed (discolored) only in the presence of magnesium ions, it is possible to easily detect and quantify magnesium ions visually. In particular, the dye compound according to exemplary embodiments of the present invention is color-developed in response to a change in the concentration of magnesium ions generated in the DNA amplification process using loop-mediated isothermal amplification (LAMP) of methicillin-resistant *Staphylococcus aureus*. Therefore, it is possible to apply the dye compound as a diagnostic reagent for visual detection to confirm the DNA amplification of methicillin-resistant *Staphylococcus aureus*. In addition, it is possible to quantify the content of magnesium ions visually by confirming the color development by reacting with dye compounds having different color crtical concentrations.

DETAILED DESCRIPTION OF EXEMPLARY EMBODIMENTS

Methicillin-resistant *Staphylococcus aureus* (MRSA) is bacteria mainly causing hospital-acquired infection such as wound infections, pneumonia, and sepsis. The MRSA is multiple drug resistant bacteria which are resistant to all β-lactam agents such as penicillin, cephalosporin, and carbapenem due to altered penicillin binding proteins (PBP 2a, PBP 2') mainly generated by a mecA gene and resistant even to other types of antimicrobial agents such as macrolide, clindamycin, tetracycline, and aminoglycoside. Accurate and rapid bacterial identification and an antimicrobial susceptibility test are required for the selection of appropriate antimicrobial agents and management of hospital-acquired infection.

As the accurate identification method of the MRSA, there are a method of directly detecting a mecA gene using a DNA probe or a polymerase chain reaction (PCR) as a molecular biological test method, a method of detecting a product of the mecA gene, PBP 2a using immunoblotting or immunoradiometric assay (IRMA), and the like. However, various conditions such as special equipments, expensive reagents, and complicated test counts and test time are not suitable to be used generally in general laboratories, and an antimicrobial susceptibility test, which has been traditionally used, requires an incubation time of 24 hours and has a difference in the expression of resistance depending on a type of culture medium or a culture condition, so that it is difficult to expect rapid and accurate results.

Accordingly, exemplary embodiments of the present invention provide a method for visually determining infection and amplification of MRSA by detecting a change in the concentration of magnesium ions by a dye compound to detect the MRSA bacteria and has an important advantage that required cost and time are remarkably low compared with the related art. Further, exemplary embodiments of the present invention use loop-mediate isothermal amplification (LAMP) without using the PCR method to amplify a gene of MRSA so that the amplification time of the gene is remarkably short.

Dyes used for detecting magnesium ions in the related art have many problems in that the color is developed (discolored) by magnesium only at a predetermined pH condition, and when the temperature or pH condition is changed, the color is developed to the same color as when magnesium exists even in the absence of magnesium ions, and thus reliability is deteriorated, and there is an inconvenience that the pH needs to be controlled every detection. Accordingly, the inventors of the present invention have developed a dye compound capable of visually confirming the presence of magnesium ions while being stable to changes in temperature and pH and dye compounds which are color-developed in a different concentration range of magnesium ions, thereby completing the present invention.

Hereinafter, the present invention will be described in more detail with reference to the following Examples. However, the following Examples should not be construed as limiting the scope of the present invention and will be described to help in the understanding of the present invention.

Synthesis Example 1. Preparation of Compound of Chemical Formula 2

2-amino-4-nitrophenol (0.385 g, 2.50 mmol, 1 eq) is dispersed in 5.8 ml of distilled water. After 0.75 g of hydrochloric acid (35%) is added, the temperature is lowered to 0° C. by adding ice. 0.19 g of sodium nitrite is added and stirred at 5° C. or lower for 1 hour, and then 0.019 g of sulfamic acid is added and stirred for 3 minutes.

After 4-hydroxynaphthalene-1-sulfonic acid (0.58 g, 2.59 mmol, 1.04 eq) is added to 9 ml of distilled water, the mixture is adjusted to pH 10 and fully dissolved, and then added to a reaction solution and stirred for 2 hours at pH 10 and 10° C. or lower.

A material obtained by filtering the reaction solution is purified by silica gel column chromatography to obtain a pure compound (128 mg, 13.2%).

$R_f$=0.4 (RP-C18, acetonitrile/water 1:2 v/v)

MALDI-TOF/MS, calculated value $C_{16}H_{11}N_3O_7S$ 389.34, measured value 388.11

Synthesis Example 2. Preparation of Compound of Chemical Formula 3

2-amino-5-nitrophenol (0.385 g, 2.50 mmol, 1 eq) is dispersed in 5.8 ml of distilled water. After 0.75 g of hydrochloric acid (35%) is added, the temperature is lowered to 0° C. by adding ice. 0.19 g of sodium nitrite is added and stirred at 5° C. or lower for 1 hour, and then 0.019 g of sulfamic acid is added and stirred for 3 minutes.

7-amino-4-hydroxynaphthaloene-2-sulfonic acid (0.628 g, 2.62 mmol, 1.05 eq) is added to 9.4 ml of distilled water and fully dissolved, and then the mixture is added to a reaction solution and stirred for 2 hours at 10° C. or lower.

A material obtained by filtering the reaction solution is purified by silica gel column chromatography to obtain a pure compound (13 mg, 1.3%).

$R_f$=0.3 (RP-C18, acetonitrile/water 1:2 v/v)

LC/MS, calculated value $C_{16}H_{12}N_4O_7S$ 404.35, measured value 403.0

Synthesis Example 3. Preparation of Compound of Chemical Formula 4

2-amino-4,6-dinitrophenol (0.498 g, 2.50 mmol, 1 eq) is dispersed in 7.4 ml of distilled water. After 0.75 g of hydrochloric acid (35%) is added, the temperature is lowered to 0° C. by adding ice. 0.19 g of sodium nitrite is added and stirred at 5° C. or lower for 1 hour, and then 0.019 g of sulfamic acid is added thereto and stirred for 3 minutes.

4-hydroxy-7-(phenylamino) naphthalene-2-sulfonic acid (0.817 g, 2.62 mmol, 1.05 eq) is added to 12.4 ml of distilled water and fully dissolved, and then the mixture is added to a reaction solution and stirred for 2 hours at 10° C. or lower.

A material obtained by filtering the reaction solution is purified by silica gel column chromatography to obtain a pure compound (45 mg, 3.4%).

$R_f$=0.4 (RP-C18, acetonitrile/water 1:2 v/v)

LC/MS, calculated value $C_{22}H_{15}N_5O_9S$ 525.45, measured value 523.9

Synthesis Examples 4 to 8: Preparation of Compounds of Chemical Formulas 5 to 9 was Synthesized in the Similar Method to Synthesis Examples 1 to 3

Synthesis Example 4. Preparation of Compound of Chemical Formula 5

(70 mg, 0.7%)

$R_f$=0.2 (RP-C18, acetonitrile/water 1:2 v/v)

LC/MS, calculated value $C_{16}H_{15}N_5O_7S$ 421.38, measured value 419.0

Synthesis Example 5. Preparation of Compound of Chemical Formula 6

(200 mg, 22.5%)

$R_f$=0.5 (RP-C18, acetonitrile/water 1:2 v/v)

LC/MS, calculated value $C_{12}H_9N_3O_8S$ 355.28, measured value 350.9

Synthesis Example 6. Preparation of Compound of Chemical Formula 7

(40 mg, 2.9%)

$R_f$=0.8 (RP-C18, acetonitrile/water 1:2 v/v)

LC/MS, calculated value $C_{22}H_{16}N_4O_{10}S_2$ 560.51, measured value 561.1

Synthesis Example 7. Preparation of Compound of Chemical Formula 8

(35 mg, 4.0%)

$R_f$=0.2 (RP-C18, acetonitrile/water 1:2 v/v)

LC/MS, calculated value $C_{16}H_{10}N_4O_6$ 354.27, measured value 352.9

Synthesis Example 8. Preparation of Compound of Chemical Formula 9

(110 mg, 9.4%)

$R_f$=0.7 (RP-C18, acetonitrile/water 1:2 v/v)

LC/MS, calculated value $C_{16}H_{10}N_3NaO_{10}S_2$ 491.38, measured value 489.8

Synthesis Example 9. Preparation of Compound DKLS of Chemical Formula 10

2-amino-4-nitrophenol-6-sulfonic acid (0.5 g, 2.14 mmol, 1 eq) is dispersed in 7.4 ml of distilled water. After 0.75 g of hydrochloric acid (35%) is added, the temperature is lowered to 0° C. by adding ice. 0.19 g of sodium nitrite is added and stirred at 5° C. or lower for 1 hour, and then 0.019 g of sulfamic acid is added and stirred for 3 minutes.

4-(benzamido)-5-hydroxynaphthalene-1,7-disulfonic acid (0.949 g, 2.24 mmol, 1.05 eq) is added to 12.4 ml of distilled water and fully dissolved, and then the mixture is added to a reaction solution and stirred for 2 hours at 10° C. or lower. A material obtained by filtering the reaction solution is purified by silica gel column chromatography to obtain a pure compound (64 mg, 4.5%).

$R_f$=0.5 (RP-C18, acetonitrile/water 1:2 v/v)

LC/MS, calculated value $C_{24}H_{16}N_4O_{14}S_3$ 668.59, measured value 667.0

Hereinafter, a method for checking the presence of magnesium ions to monitor an amplification process of MRSA bacteria using the loop-based isothermal amplification method (LAMP) using the dye compounds will be described using specific Examples. It is apparent that the scope of the present invention is not limited to the following Examples.

<Selection of Dye Compounds>

1) Synthesis of Candidate Substances

Compounds developed by magnesium ions through a compound library were screened, 70 types of candidate compounds were synthesized based on the screened compounds, and the candidate substances were selected through solubility and spectroscopic analysis and further modeled based on the structure of the selected compounds to finally obtain 9 types of compounds such as compounds of Chemical Formulas 2 to 9 and DKLS.

2) Solubility Test

The solubility in water was measured to confirm the solubility of the synthesized candidate compounds. Specifically, 10 mg of hydroxynaphthalene blue (HNB), which is a compound known to be developed by magnesium ions as a control, and 10 mg of each of the candidate compounds were dissolved in 1 ml of deionized water, and then the solubility was confirmed. It was confirmed that the 9 types of compounds among 70 types of the candidate compounds and hydroxynaphthalene blue were dissolved in water. As a result, the 9 types of compounds showed excellent solubility in water.

<Evaluation of Color Development Characteristics>

1) Preparation of Solution 200 mM of a magnesium chloride solution was prepared by dissolving 0.9521 g of magnesium chloride in 50 ml of deionized water.

59.99 mg of sodium phosphate monobasic and 70.98 mg of sodium phosphate dibasic were dissolved in 50 ml of distilled water to prepare 10 mM of a sodium phosphate buffer solution, and then 28.85 ml of a sodium phosphate monobasic solution and 21.15 ml of a sodium phosphate dibasic solution were mixed to prepare a sodium phosphate buffer solution at pH 7. In a similar manner, the two solutions were mixed to prepare sodium phosphate buffer solutions having acidity of pH 4, pH 7, pH 9, and pH 11, respectively.

For determination of color development, the HNB and the candidate substance were prepared at concentrations of 240 µM and used for the test.

2) Preparation of Specimen

Hydroxynaphthalene blue (HNB) and 9 types of water-soluble candidate substances selected by the solubility test were diluted with distilled water to prepare specimens at concentrations of 240 µM, respectively.

3) Evaluation of Magnesium Ion Detection Characteristics and pH Stability

It was confirmed whether the candidate substances according to the present invention reacted with magnesium ions to be color-developed (discolored). In addition, pH stability was confirmed according to whether the candidate substances were specifically color-developed by reacting only with magnesium ions regardless of a pH change.

The color development of the control (HNB) and 35 types of candidate substances was confirmed under conditions of blank, a $MgCl_2$ solution, pH 4, pH 7, pH 9, and pH 11 using a 96 well plate (12×6 holes). Specifically, 100 µl of deionized water (blank) was added in a first row of the plate, 100 µl of the $MgCl_2$ solution was added in a second row thereof, and 100 µl of each of solutions at pH 4, pH 7, pH 9, and pH 11 was added in third to sixth rows thereof using 10 mM of the sodium phosphate buffer solution prepared in step a) above. In columns of the plate, 100 µl of specimens prepared at a concentration of 240 µM were added to 6 rows, respectively, and a total of 36 specimens were screened. The final concentration of the $MgCl_2$ solution contained in each well was 100 mM and the final concentration of the specimen was 120 µM.

Each specimen showed a unique color in the deionized water (blank), and 9 types of compounds color-developed (discolored) in the presence of 200 mM $MgCl_2$ were confirmed.

In particular, the compounds of Chemical Formulas 3 and 4 were developed to a complementary color to be clearly distinguished from the blank in the presence of magnesium ions, and were developed to other colors completely different from the developed color in the presence of magnesium ion even in a pH change, and as a result, it was confirmed that the pH stability was excellent.

The compound of Chemical Formula 3 was developed to orange or violet in the absence of magnesium ions, but was developed to dark blue only in the presence of magnesium. The compound of Chemical Formula 4 was developed to red in the absence of magnesium ions, but was developed to dark violet only in the presence of magnesium. As a result, there was a clear difference therebetween. On the other hand, it was evaluated that the compound of Chemical Formula 2 was developed to a color clearly different from that in the presence of magnesium ions under neutral to basic conditions, and had characteristics similar to those of the control HNB.

On the other hand, hydroxynaphthalene blue (HNB), a representative color developing agent that was developed in the presence of magnesium ions, was discolored (developed) to a color similar to that in the presence of magnesium ions even in an acidity range of pH 7 to 11 in the absence of magnesium ions. Therefore, it was confirmed that the hydroxynaphthalene blue had a problem that it was inconvenient to control the specimen to be acidic, specifically around pH 4, in order to detect magnesium ions, and the reliability was lowered.

Through the test, it was confirmed that the compounds of Chemical Formula 3 and 4 were dye compounds which were particularly effective for the detection of magnesium ions by being developed at a specific wavelength only in the presence of magnesium ions without being influenced by the pH change.

4) Evaluation of Temperature Stability

It was confirmed whether the candidate substances according to the present invention had color changes depending on the temperature. 100 µl of the specimens (HNB and 35 types of candidate substances) prepared in step 2) and 100 µl of the deionized water were added into a 1.5 ml tube (final volume of 200 µl, final specimen concentration of 120 µM). After diluting well at room temperature, the color developed state was photographed, the mixture was incubated at 80° C. for 12 hours, and then the color change was observed.

As a result of the test, the specimens according to exemplary embodiments of the present invention were not influenced by the temperature and the colors were preserved.

5) Evaluation of Molar Absorption Coefficient

HNB and 9 types of candidate substances were dissolved in deionized water to prepare 100 µg/ml of a stock and then diluted with deionized water to prepare samples of 50, 25 and 12.5 µg/ml. Next, an absorption spectrum was obtained using an analyzer UV-vis spectrometer (Agilent 8453), and then absorption coefficient values at a concentration of 10 mg/ml were measured and shown in Table 1 below.

| No. | Compound | Molar absorption coefficient |
|---|---|---|
| 1 | HNB | 13,000 |
| 2 | Chemical Formula 2 | 12,000 |
| 3 | Chemical Formula 3 | 44,000 |
| 4 | Chemical Formula 4 | 31,000 |
| 5 | Chemical Formula 5 | 33,579 |
| 6 | Chemical Formula 6 | 18,000 |
| 7 | Chemical Formula 7 | 25,000 |
| 8 | Chemical Formula 8 | 5,117 |
| 9 | Chemical Formula 9 | 23,000 |

As shown in Table 1, it was confirmed that the compound of Chemical Formula 3 had the highest molar absorption coefficient of 44,000 and an absorption coefficient 3.38 times higher than that of HNB, and the compound of Chemical Formula 4 had an absorption coefficient of 31,000, which was 2.38 times higher than that of HNB, and thus it was evaluated that the compounds were industrially useful.

<Evaluation of Magnesium Ion Sensitivity>

1) Evaluation of Magnesium Ion Sensitivity at Concentration of Less than 10 mM

Through the evaluation, the compounds of Chemical Formulas 2, 3, and 4 were selected as excellent dye compounds for detecting magnesium ions. The sensitivities of the selected 4 types of compounds and HNB for detecting magnesium ions were evaluated.

Magnesium chloride was dissolved in deionized water and diluted to 8, 10, 12, 14 and 16 mM, respectively, to prepare specimens. Next, as the dye compounds, the HNB and the compound of Chemical Formula 2 were prepared at a concentration of 240 μM, but the compounds of Chemical Formulas 3 and 4 were prepared to be diluted at a concentration of 120 μM by 50% because the molar absorption coefficient of the compounds was two times higher than that of the control (HNB).

In each row of a 96-well plate, 1 ml of the dye compound was filled, and in each column, 1 ml of a diluted magnesium chloride solution was filled, and then the color changes were observed and absorbance was measured. The final concentrations of magnesium chloride in the 96-well plate were 0, 4, 5, 6, 7, and 8 mM, and the final concentrations of HNB and Chemical Formula 2 were 120 μM, respectively, and the final concentrations of Chemical Formulas 3 and 4 were 60 μM, respectively.

The compound of Chemical Formula 3 exhibited a complementary color by detecting magnesium ions contained in a magnesium chloride solution diluted to a very low concentration of 4 mM, and thus the sensitivity to magnesium ions was very excellent. Therefore, detection of a small amount of magnesium ions is easy, and the industrial availability is very high.

It was observed that in the dye compound represented by Chemical Formula 3 according to exemplary embodiments of the present invention, the absorption spectrum was shifted from 500 nm to 640 nm by magnesium ions. In addition, since the absorbance change is remarkable with respect to the magnesium ion concentration, magnesium contained in the measurement specimen may be quantitatively calculated through the absorbance evaluation.

2) Evaluation of Magnesium Ion Sensitivity at Concentration of 10 mM or More

In order to evaluate the magnesium ion sensitivity for the HNB, and Chemical Formulas 2 and 4 which were not discolored at the magnesium ion concentration of less than 10 mM, an additional test was conducted in the same manner at a concentration of 10 mM or more. The magnesium concentration in the 96 well plate was confirmed from 10 mM to 100 mM, and the final concentration of the dye compound was set to 120 μM.

The HNB started to be color-developed at a concentration of 10 mM or more, developed to violet at 20 to 30 mM, and developed to dark blue at 40 mM or more, the compound of Chemical Formula 2 was remarkably developed to cherry red instead of violet at 100 mM or more, and the compound of Chemical Formula 4 started to be developed from red purple to purple at a concentration of 10 mM and developed to blue violet at a concentration of about 20 mM.

As in the test, the compound according to exemplary embodiments of the present invention reacts with magnesium ions to be discolored (developed) by shifting the absorption spectrum, and the lowest detection concentration of magnesium ions varies depending on the structure of the compound. Accordingly, the compounds having different lowest detection concentrations of magnesium ions according to exemplary embodiments of the present invention are treated to samples to be measured, and the concentration of magnesium ions contained in the samples may be visually confirmed by confirming the color development and the developed colors of the samples.

Example 1: Selection of Compounds for Configuring Methicillin-Resistant *Staphylococcus aureus* (MRSA) Detection Kit In Example 1, a mecA gene was selected as a target gene for detecting MRSA, and six primers of the mecA gene shown in Table 2 below were prepared.

TABLE 2

<MRSA primer sequence>

| Oligomer name | Base sequence |
|---|---|
| F3 | ATG ATT ATG GCT CAG GTA CTG |
| B3 | AAC CCA ATC ATT GCT GTT AAT ATT |
| FIP | TAC ATA AAT GGA TAG ACG TCA TCT ATC CAC CCT CAA ACA GGT G |
| BIP | GGC ATG AGT AAC GAA GAA TAT AAT CCT GGT GAA GTT GTA ATC TGG AAC |
| LF | ATG AAG GTG TGC TTA CAA GTG C |
| LB | CCG AAG ATA AAA AAG AAC CTC TGC T |

1) Selection of Compound According to Solubility Test and Magnesium Sensitivity

Various color developing dyes represented by Chemical Formula 1 above were dissolved in distilled water (D.W) and the solubility was tested to select a compound having high solubility. The selected compound was diluted at each concentration (100 uM, 50 uM, 25 uM, 12.5 uM, 6.25 uM, and 3.13 uM) and the reaction sensitivity with magnesium (magnesium concentration of 100 mM, 10 mM) by concentration was tested.

Figure 1:
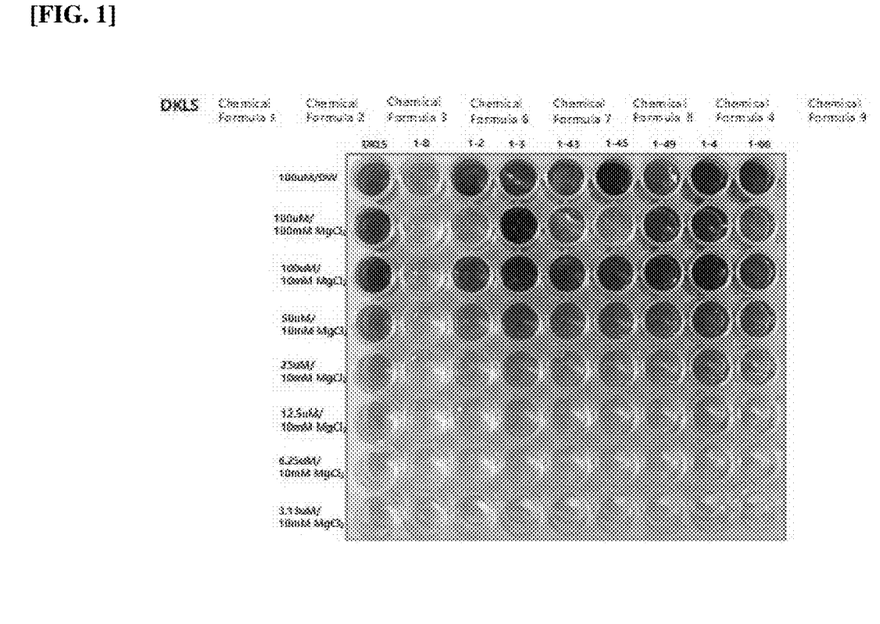
FIG. 1 illustrates results of evaluating the solubility and the sensitivity to magnesium ions of 9 types of compounds used in exemplary embodiments of the present invention.

As a result of the test, 9 types of compounds which had high solubility in D.W and sensitively reacted with magnesium were selected. FIG. 1 illustrates the selected 9 types of compounds (Chemical Formulas 2 to 9 and DKLS).

2) Detection of Methicillin-Resistant *Staphylococcus aureus* (MRSA) Using Loop-Mediated Isothermal Amplification (LAMP).

Figure 2:
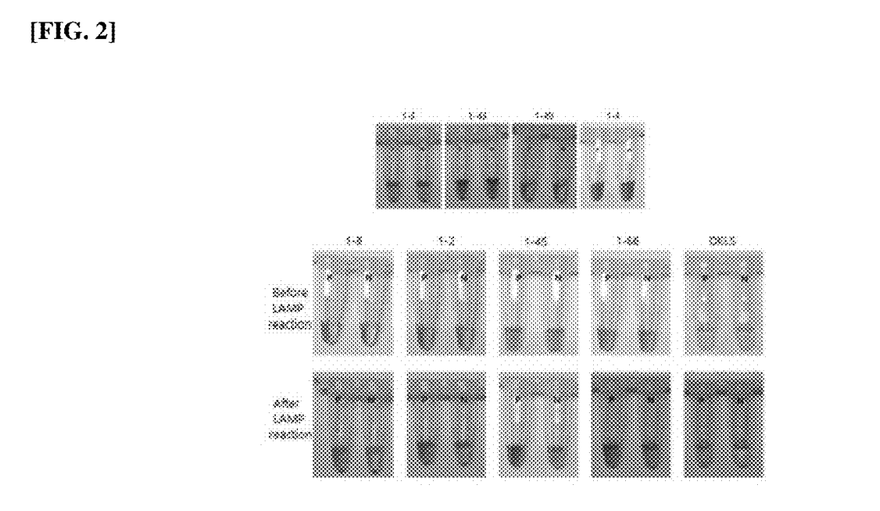
FIG. 2 illustrates results of evaluating color development according to the presence of MRSA by loop-mediated isothermal amplification (LAMP) of the compounds in accordance with exemplary embodiments of the present invention. Herein, P represents a positive control and N represents a negative control.

Detection of MRSA was performed with respect to 9 types of compounds using loop-mediated isothermal amplification (LAMP). The LAMP has a cycle of enzymatic inactivation at 80° C. for 5 minutes after reaction at 63° C. for 30 minutes and is performed by reaction for total 35 minutes. After the LAMP, as illustrated in FIG. 2, in 4 types of compounds (Chemical Formulas 3, 4, 6, and 8), the changes were not observed, and in 5 types of compounds (Chemical Formulas 2, 5, 7, and 9, and DKLS), changes in color development were observed. It was confirmed that in the 5 types of compounds (Chemical Formulas 2, 5, 7, and 9, and DKLS), the MRSA detection is enabled using the LAMP.

Figure 3:
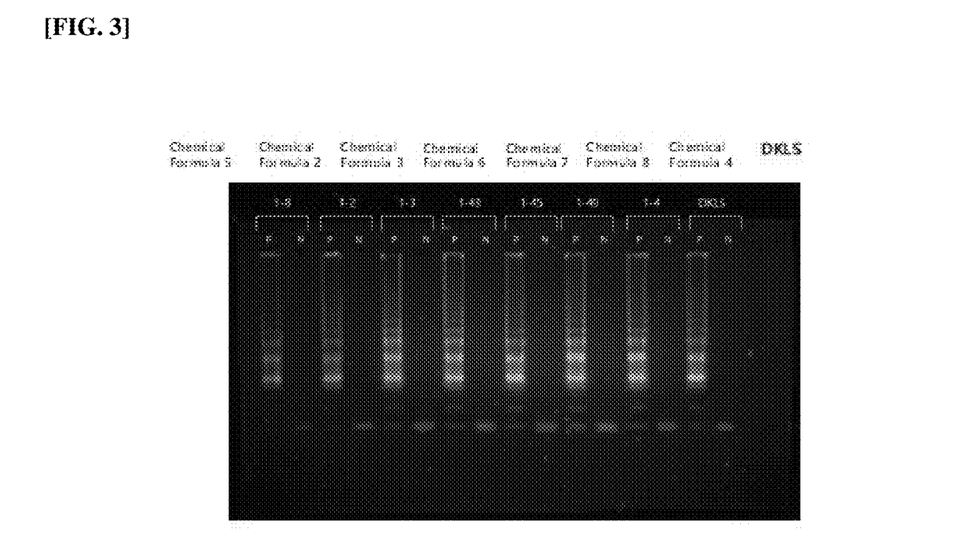
FIG. 3 illustrates results of confirming the amplification of MRSA DNA by electrophoresis. Herein, P represents a positive control and N represents a negative control.

After confirming the color changes of the compounds, as a result of confirming the amplification of MRSA using a DNA electrophoresis method to confirm accurate MRSA amplification, as illustrated in FIG. 3, it was confirmed that in a positive control, the MRSA amplification was performed and in a negative control, the MRSA amplification was not performed. It was confirmed that in the compounds without color change, the MRSA amplification was performed and there was only no color change.

3) Detection Sensitivity Test of Methicillin-Resistant *Staphylococcus aureus* (MRSA) Using Loop-Mediated Isothermal Amplification (LAMP).

Figure 4:
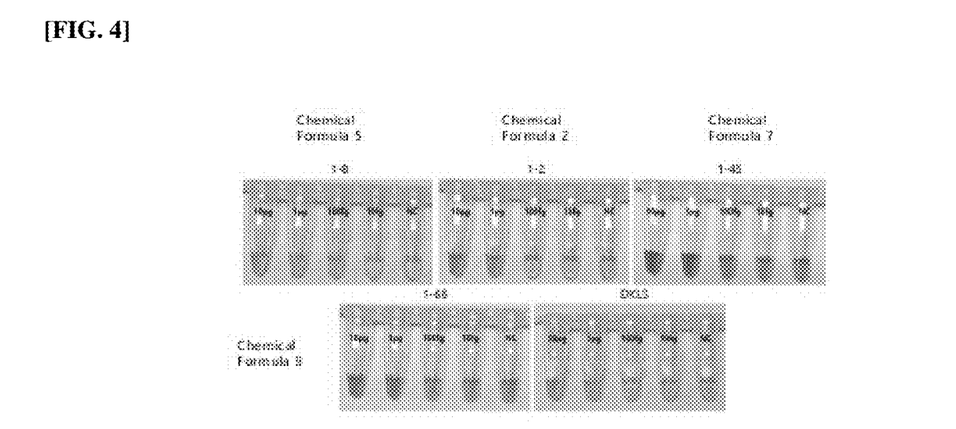
FIG. 4 illustrates results of evaluating sensitivity to MRSA DNA of the compounds in accordance with exemplary embodiments of the present invention by loop-mediated isothermal amplification (LAMP). Herein, NC represents a negative control.

The sensitivity test of the selected 5 types of compounds was performed using LAMP. MRSA DNA was diluted 10-fold to be made at concentrations of 10 pg, 1 μg, 100 fg, and 10 fg, and then the sensitivity test was performed using the LAMP, and at this time, the concentrations of 5 types of compounds were the same as each other. As illustrated in FIG. 4, detection of up to 1 μg of DNA was enabled by all of the 5 types of compounds and detection of up to 100 fg of DNA was enabled by the compound of Chemical Formula 5.

4) Selection of Color Developing Dyes Constituting Kit

Based on the results of the test of Example 1, compounds for constituting a MRSA detection kit were finally selected. The detection of up to 100 fg of MRSA is enabled by the compound of Chemical Formula 5, but it was confirmed that there was a problem that errors in detection during visual observation were caused due to color change. Therefore, a compound of Chemical Formula 7 which was easy to be visually detected due to a clear color change and can detect 1 μg of MRSA was selected.

Example 2: Comparative Verification of Detection Sensitivity

1) Comparative Verification of Detection Sensitivity of Methicillin-Resistant *Staphylococcus aureus* (MRSA) Using Loop-Mediated Isothermal Amplification (LAMP)

Figure 5:
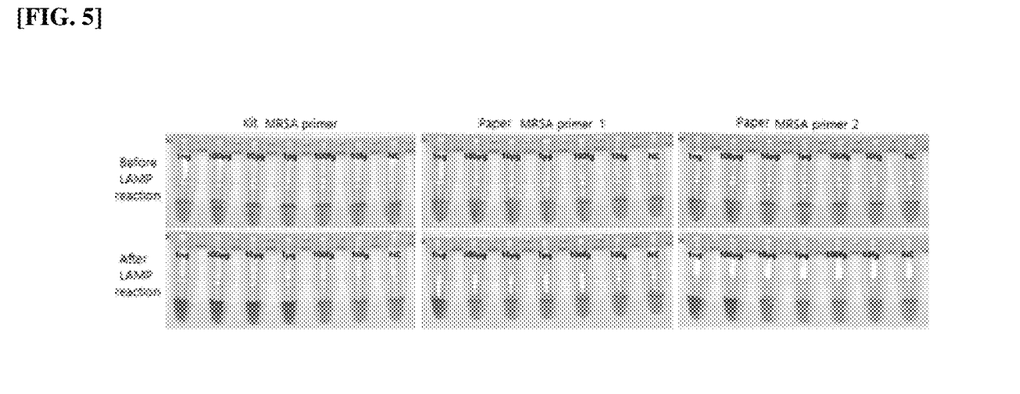
FIG. 5 illustrates results of evaluating color development of a compound of Chemical Formula 7 to MRSA DNA. Herein, NC represents negative control.

The excellence of a kit-constituting primer was verified by comparing a kit-constituting MRSA primer according to exemplary embodiments of the present invention and a primer reported in the paper (Yoshiki Misawa et al. 2007. Application of loop-mediated isothermal amplification technique to rapid and direct detection of methicillin-resistant *Staphylococcus aureus* in blood cultures. J infect Chemother. 13:134-14). The selected compound of Chemical Formula 7 was used and the MRSA DNA was diluted 10-fold to be made at concentrations of 1 ng, 100 μg, 10 μg, 1 μg, 100 fg, and 10 fg, respectively, and the comparative verification was performed by the LAMP reaction. As illustrated in FIG. 5, the kit-constituting MRSA primer was able to detect 1 μg of MRSA DNA. On the other hand, in the case of two types of MRSA primers reported in the paper, MRSA DNA was detected up to 1 ng by Primer 1 and 100 μg by Primer 2.

In addition, comparative verification with a PCR method in the related art was performed. The excellence of exemplary embodiments of the present invention was verified by comparing a primer disclosed in the paper (Duarte C. Oliveira and Herminia de Lencastre. 2002. Multiplex PCR Strategy for Rapid Identification of Structural Types and Variants of the mec Element in Methicillin-Resistant *Staphylococcus aureus*. Antimicrob Agents Chemother. 46(7): 2155-61) with a PCR method. MRSA DNA was diluted 10-fold to be made at concentrations of 10 ng, 1 ng, 100 μg, 10 μg, 1 μg, 100 fg, and 10 fg, and the same amount was added and reacted in the PCR method and the LAMP.

Figure 6:
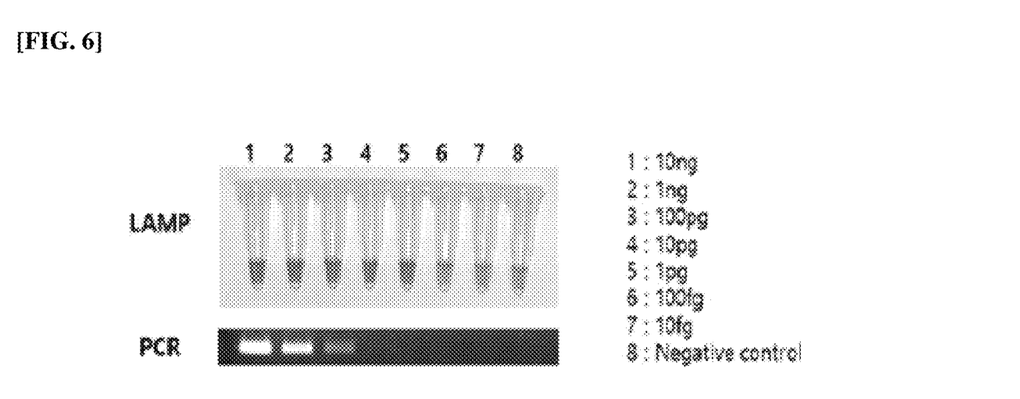
FIG. 6 illustrates results of confirming sensitivities in detecting MRSA according to an exemplary method of the present invention and detecting MRSA using a PCR reaction in the related art.

As the test result, in the method of detecting MRSA using exemplary embodiments of the present invention, a total of required time was about 35 minutes and MRSA was able to be detected up to 1 μg. On the contrary, when using the PCR method in the related art, a total of required time was about 2 hours and MRSA was detected up to 100 μg. As a result, it was confirmed that the kit of exemplary embodiments of the present invention was able to confirm the infection with MRSA more efficiently than the related art, and the result was illustrated in FIG. 6.

The invention claimed is:

1. A kit for diagnosing an infection caused by Methicillin-Resistant *Staphylococcus aureus* (MRSA) through a change in a concentration of magnesium ions, the kit comprising: a dye compound selected from at least one of compounds represented by the following Chemical Formulas 3, 4, 7, and 9:

Chemical Formula 3

Chemical Formula 4

Chemical Formula 7

Chemical Formula 9

2. The kit of claim 1, wherein the MRSA is amplified by loop-mediate isothermal amplification (LAMP).

3. A method for diagnosing an infection caused by Methicillin-Resistant *Staphylococcus aureus* (MRSA) through loop-mediate isothermal amplification (LAMP) using at least one of compounds represented by the following Chemical Formulas 3, 4, 7, and 9, wherein each of the compounds represented by Chemical Formulas 3, 4, 7, and 9 forms a complex with magnesium in a LAMP reaction solution and color-developed wavelengths of the dye compounds represented by Chemical Formulas 3, 4, 7, and 9 are changed by a change in a magnesium concentration generated in the LAMP reaction process.

Chemical Formula 3

Chemical Formula 7

Chemical Formula 4

Chemical Formula 9

* * * * *